(12) United States Patent
McIntosh et al.

(10) Patent No.: US 6,767,896 B1
(45) Date of Patent: Jul. 27, 2004

(54) CONOTOXIN PEPTIDES

(75) Inventors: J. Michael McIntosh, Salt Lake City, UT (US); Baldomero M. Olivera, Salt Lake City, UT (US); Lourdes J. Cruz, Manila (PH); Gloria P. Corpuz, Miliani, HI (US); Robert M. Jones, Salt Lake City, UT (US); James E. Garrett, Salt Lake City, UT (US)

(73) Assignees: Cognetix, Inc., Salt Lake City, UT (US); University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/580,201

(22) Filed: May 26, 2000

Related U.S. Application Data

(63) Continuation-in-part of application No. 09/493,143, filed on Jan. 28, 2000.
(60) Provisional application No. 60/173,298, filed on Dec. 28, 1999, and provisional application No. 60/118,381, filed on Jan. 29, 1999.

(51) Int. Cl.[7] .................... A61K 38/08; A61K 38/10; C07K 7/08; C07K 7/06; C07K 14/435
(52) U.S. Cl. ............... 514/14; 514/2; 514/14; 514/15; 530/324; 530/327; 530/300
(58) Field of Search ................ 530/324, 327, 530/300; 514/2, 15, 14, 16

(56) References Cited

U.S. PATENT DOCUMENTS 5,885,797 A * 3/1999 Chen et al. ............. 435/69.1

FOREIGN PATENT DOCUMENTS

WO        0020444        4/2000

OTHER PUBLICATIONS

McIntosh, J.M. (1999) "Conus Peptides as Probes for Ion Channels", Methods in Enzymology, vol. 294: 605–624.
McIntosh, J.M. (1999) "Conus Peptides Targeted to Specific Nicotinic Acetylcholine Receptor Subtypes", Annual Rev. Biochemistry, vol. 68:59–88.
McIntosh, J.M. et al. (2000) "Isolation and Characterization of a novel conus peptide with apparent antinociceptive activity", Journal of Biol. Chemistry, Jul. 2000, pp. 1–31 w/ 6 pg appendix.
Olivera, B.M. et al. (1985). "Peptide Neurotoxins from Fish–Hunting Cone Snails," Science 230:1338–1343.
Olivera, B.M. et al. (1990). "Diversity of Conus Neuropeptides," Science 249:257–263.
Sawynok, J. et al., (Aug. 1999) Pain 82(2): 149–158 (hereinafter "Sawynok, et al.").
Ardid, D. et al., (1992) Fund. Clin. Pharmacology 6(2): 75–82 (hereinafter "Ardid, et al.").
Kawamata, et al., (Sep. 1999) Br. J. Anaesth 83(3): 449–452 (hereinafter "Kawamata, et al.").
Reimann, et al., (Jan. 1999) Anesth Analg 88(1): 141–145 (hereinafter "Reimann, et al.").
Yaksh, T.L. (1985) Pharmacology Biochemistry & Behavior 22: 845–858 (hereinafter "Yaksh I").
Yaksh T.L. & Takano, Y. (1992) J. Pharmacology & Experimental Therapeutics 261(2): 764–772 (hereinafter "Yaksh II").
Yaksh, T.L. & Howe, J.R. (1982) J. Pharmacology & Experimental Therapeutics 220(2): 311–321 (hereinafter "Yaksh III").
Howe, J.R., et al. (1983) J. Pharmacology & Experimental Therapeutics 224(3): 552–558 (hereinafter "Howe, et al.").
Solomon, et al., (1989) J. Pharmacology & Experimental Therapeutics 251(1): 28–38 (hereinafter "Solomon, et al.").
Fleetwood–Walker, S.M. et al., (1985) Brain Research 334: 243–254 (hereinafter "Fleetwood–Walker, et al.").
International Application WO 00/20444, published Apr. 13, 2000 (hereinafter International Application WO 00/20444).

* cited by examiner

Primary Examiner—Gabriele Bugaisky
(74) Attorney, Agent, or Firm—Rothwell Figg Ernst & Manbeck

(57) ABSTRACT

The invention relates to relatively short conotoxin peptides, about 10–20 residues in length as described herein, which are naturally available in minute amounts in the venom of the cone snails or analogous to the naturally available peptides, and which preferably include two disulfide bonds. These conotoxin peptides have analgesic activity and are thus useful for treating or preventing pain.

24 Claims, No Drawings

CONOTOXIN PEPTIDES

CROSS-REFERENCE TO RELATED APPLICATIONS

The present application is a continuation-in-part application of U.S. patent application Ser. No. 09/493,143 filed 28 Jan. 2000, incorporated herein by reference. The present application is also related to U.S. provisional patent applications Serial No. 60/118,381, filed 29 Jan. 1999 and Ser. No. 60/173,298, filed 28 Dec. 1999, each incorporated herein by reference.

This invention was made with Government support under Grant Nos. GM48677 and MH5363 1 awarded by the National Institute of General Medical Sciences, National Institutes of 8) Health, Bethesda, Md. The United States Government has certain rights in the invention.

BACKGROUND OF THE INVENTION

The invention relates to relatively short conotoxin peptides, about 10–20 residues in length, which are naturally available in minute amounts in the venom of the cone snails or analogous to the naturally available peptides, and which preferably include two disulfide bonds. These conotoxin peptides have analgesic activity and are thus useful for treating or preventing pain.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Conus is a genus of predatory marine gastropods (snails) which envenomate their prey. Venomous cone snails use a highly developed projectile apparatus to deliver their cocktail of toxic conotoxins into their prey. In fish-eating species such as *Conus magus* the cone detects the presence of the fish using chemosensors in its siphon and when close enough extends its proboscis and fires a hollow harpoon-like tooth containing venom into the fish. This immobilizes the fish and enables the cone snail to wind it into its mouth via an attached filament. For general information on Conus and their venom see the website "grimwade.biochem" at "unimelb.edu.au" Prey capture is accomplished through a sophisticated arsenal of peptides which target specific ion channel and receptor subtypes. Each Conus species venom appears to contain a unique set of 50–200 peptides. The composition of the venom differs greatly between species and between individual snails within each species, each optimally evolved to paralyze its prey. The active components of the venom are small peptides toxins, typically 12–30 amino acid residues in length and are typically highly constrained peptides due to their high density of disulphide bonds.

The venoms consist of a large number of different peptide components that when separated exhibit a range of biological activities: when injected into mice they elicit a range of physiological responses from shaking to depression. The paralytic components of the venom that have been the focus of recent investigation are the α-, ω- and μ-conotoxins. All of these conotoxins act by preventing neuronal communication, but each targets a different aspect of the process to achieve this. The α-conotoxins target nicotinic ligand gated channels, the μ-conotoxins target the voltage-gated sodium channels and the ω-conotoxins target the voltage-gated calcium channels (Olivera et al., 1985). For example a linkage has been established between α-, αA-& φ-conotoxins and the nicotinic ligand-gated ion channel; ω-conotoxins and the voltage-gated calcium channel; μ-conotoxins and the voltage-gated sodium channel; δ-conotoxins and the voltage-gated sodium channel; κ-conotoxins and the voltage-gated potassium channel; conantokins and the ligand-gated glutamate (NMDA) channel. For a partial list of Conus peptides and their amino acid sequences see the website "pir" at "georgetown.edu".

However, the structure and function of only a small minority of these peptides have been determined to date. For peptides where function has been determined, three classes of targets have been elucidated: voltage-gated ion channels; ligand-gated ion channels, and G-protein-linked receptors.

Conus peptides which target voltage-gated ion channels include those that delay the inactivation of sodium channels, as well as blockers specific for sodium channels, calcium channels and potassium channels. Peptides that target ligand-gated ion channels include antagonists of NMDA and serotonin receptors, as well as competitive and noncompetitive nicotinic receptor antagonists. Peptides which act on G-protein receptors include neurotensin and vasopressin receptor agonists. The unprecedented pharmaceutical selectivity of conotoxins is at least in part defined by a specific disulfide bond frameworks combined with hypervariable amino acids within disulfide loops (for a review see McIntosh et al., 1998).

There are drugs used in the treatment of pain, which are known in the literature and to the skilled artisan. See, for example, Merck Manual, 16th Ed. (1992). However, there is a demand for more active analgesic agents with diminished side effects and toxicity and which are non-addictive. The ideal analgesic would reduce the awareness of pain, produce analgesia over a wide range of pain types, act satisfactorily whether given orally or parenterally, produce minimal or no side effects, be free from tendency to produce tolerance and drug dependence.

Due to the high potency and exquisite selectivity of the conopeptides, several are in various stages of clinical development for treatment of human disorders. For example, two Conus peptides are being developed for the treatment of pain. The most advanced is ω-conotoxin MVIIA (ziconotide), an N-type calcium channel blocker (see Heading, C., 1999; U.S. Pat. No. 5,859,186). ω-Conotoxin MVIIA, isolated from *Conus magus*, is approximately 1000 times more potent than morphine, yet does not produce the tolerance or addictive properties of opiates. ω-Conotoxin MVIIA has completed Phase III (final stages) of human clinical trials and is now awaiting U.S. Food and Drug Administration approval as a therapeutic agent. ω-Conotoxin MVIIA is introduced into human patients by means of an implantable, programmable pump with a catheter threaded into the intrathecal space. Preclinical testing for use in post-surgical pain is being carried out on another Conus peptide, contulakin-G, isolated from *Conus geographus* (Craig et al. 1999). Contulakin-G is a 16 amino acid O-linked glycopeptide whose C-terminus resembles neurotensin. It is an agonist of neurotensin receptors, but appears significantly more potent than neurotensin in inhibiting pain in in vivo assays.

In view of a large number of biologically active substances in Conus species it is desirable to further characterize them and to identify peptides having many of the characteristics of an ideal analgesic for the treatment of pain. Surprisingly, and in accordance with this invention, Applicants have discovered novel conotoxins that can be useful for the treatment of pain and could address a long felt need for a safe and effective treatment.

SUMMARY OF THE INVENTION

The invention relates to relatively short conotoxin peptides, about 10–20 residues in length, which are naturally available in minute amounts in the venom of the cone snails or analogous to the naturally available peptides, and which preferably include two disulfide bonds. These conotoxin peptides have analgesic activity and are thus useful for treating or preventing pain.

In one embodiment, the present invention reports the isolation and characterization of a peptide from venom of Conus species such as marble cone, Conus marmoreus, that represents a new class of peptides and that possesses analgesic properties. In a second embodiment, related conotoxin peptides are isolated by DNA cloning. This invention provides isolation and characterization of a new class of peptides from the venom of the cone snails. The specific example of an isolated peptide is a representative member of a new family of Conus peptides.

More specifically, the present invention is directed to conotoxin peptides having the general formula I:

Xaa-Xaa$_0$-Xaa$_1$-Cys-Cys-Gly-Xaa$_2$-Xaa$_3$-Xaa$_4$-Cys-Xaa$_5$-Xaa$_6$-Cys-Xaa$_7$ (SEQ ID NO:1)

wherein Xaa is des-Xaa, Asn, Gln or pyro-Glu; Xaa$_0$ is des-Xaa$_0$, Gly, Ala, Glu, γ-carboxy-Glu (Gla), Asp, Asn, Ser, Thr, g-Asn (where g is glycosylation), g-Ser or g-Thr; Xaa$_1$ is Val, Ala, Gly, Leu, Ile, Ser, Thr, g-Asn, g-Ser or g-Thr; Xaa$_2$ is Phe, Tyr, meta-Tyr, ortho-Tyr, nor-Tyr, mono-halo-Tyr, di-halo-Tyr, O-sulpho-Tyr, O-phospho-Tyr, nitro-Tyr, Trp (D or L), neo-Trp, halo-Trp (D or L), any synthetic aromatic amino acid, an aliphatic amino acid bearing linear or branched saturated hydrocarbon chains such as Leu (D or L), lie and Val or non-natural derivatives of the aliphatic amino acid; Xaa$_3$ is Lys, Arg, homolysine, homoarginine, ornithine, nor-Lys, His, N-methyl-Lys, N,N'-dimethyl-Lys, N,N',N"-trimethyl-Lys, any synthetic basic amino acid, Ser, Thr, g-Ser, g-Thr or any hydroxylated synthetic residue; Xaa$_4$ is an aliphatic amino acids bearing linear or branched saturated hydrocarbon chains such as Leu (D or L), Ile and Val or non-natural derivatives of the aliphatic amino acid, Met, Phe, Tyr, meta-Tyr, ortho-Tyr, nor-Tyr, mono-halo-Tyr, di-halo-Tyr, O-sulpho-Tyr, O-phospho-Tyr, nitro-Tyr, Trp (D or L), neo-Trp, halo-Trp (D or L) or any synthetic aromatic amino acid; Xaa$_5$ is His, Ser, Thr, g-Ser, g-Thr, an aliphatic amino acid bearing linear or branched saturated hydrocarbon chains such as Leu (D or L), Ile and Val, non-natural derivatives of the aliphatic amino acid, Phe, Tyr, meta-Tyr, ortho-Tyr, nor-Tyr, mono-halo-Tyr, di-halo-Tyr, O-sulpho-Tyr, O-phospho-Tyr, nitro-Tyr, Trp (D or L), neo-Trp, halo-Trp (D or L) or a synthetic aromatic amino acid; Xaa$_6$ is Pro, hydroxy-Pro (Hyp) or g-Hyp; Xaa$_7$ is des-Xaa$_7$, Gly, Ala, Lys, Arg, homolysine, homoarginine, ornithine, nor-Lys, His, N-methyl-Lys, N,N'-dimethyl-Lys, N,N',N"-trimethyl-Lys or any synthetic basic amino acid. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic amino acid, e.g., tetrazolyl derivatives of Gly and Ala. The nonnatural derivatives of the aliphatic amino acids include those synthetic derivatives bearing non-natural aliphatic branched or linear side chains C$_n$H$_{2n+2}$ up to and including n=8. The halogen is iodo, chloro, fluoro or bromo; preferably iodo for halogen substituted-Tyr and bromo for halogen-substituted Trp.

The present invention is also directed to novel specific conotoxin peptides within general formula I having the formulas:

Asn-Gly-Val-Cys-Cys-Gly-Xaa$_1$-Xaa$_2$-Leu-Cys-His-Xaa$_3$-Cys (SEQ ID NO:2);

Gly-Val-Cys-Cys-Gly-Xaa$_1$-Xaa$_2$-Leu-Cys-His-Xaa$_3$-Cys (SEQ ID NO:3);

Gly-Ile-Cys-Cys-Gly-Val-Ser-Phe-Cys-Xaa$_1$-Xaa$_3$-Cys (SEQ ID NO:4);

Ala-Cys-Cys-Gly-Xaa$_1$-Xaa$_2$-Leu-Cys-Ser-Xaa$_3$-Cys (SEQ ID NO:5);

Xaa$_4$-Thr-Cys-Cys-Gly-Xaa$_1$-Arg-Met-Cys-Val-Xaa$_3$-Cys-Gly (SEQ ID NO:6); and Ser-Thr-Cys-Cys-Gly-Phe-Xaa$_2$-Met-Cys-Ile-Xaa$_3$-Cys-Arg (SEQ ID NO:7), wherein Xaa$_1$ is Tyr, mono-halo-Tyr, di-halo-Tyr, O-sulpho-Tyr, O-phospho-Tyr, nitro-Tyr; Xaa$_2$ is Lys, N-methy-Lys, N,N-dimethyl-Lys or N,N,N-trimethyl-Lys; Xaa$_3$ is Pro or hydroxy-Pro (Hyp), preferably hydroxy-Pro; Xaa$_4$ is Gln or pyro-Glu; and the C-terminus contains a carboxyl or amide group. The halo is preferably chlorine or iodine, more preferably iodine. In addition, the Arg residues may be substituted by Lys, ornithine, homoarginine, nor-Lys, N-methyl-Lys, N,N-dimethyl-Lys, N,N,N-trimethyl-Lys or any synthetic basic amino acid; the Xaa$_2$ residues may be substituted by Arg, ornithine, homoargine, nor-Lys, or any synthetic basic amino acid; the Tyr residues may be substituted with any synthetic aromatic containing amino acid; the Ser residues may be substituted with Thr or any synthetic hydroxy containing amino acid; the Thr residues may be substituted with Ser or any synthetic hydroxy containing amino acid; the Phe and Trp residues may be substituted with any synthetic aromatic amino acid; and the Asn, Ser, Thr or Hyp residues may be glycosylated. The Cys residues may be in D or L configuration and may optionally be substituted with homocysteine (D or L). The Tyr residues may also be substituted with the 3-hydroxyl or 2-hydroxyl isomers (meta-Tyr or ortho-Tyr, respectively) and corresponding O-sulpho- and O-phospho-derivatives. The acidic amino acid residues may be substituted with any synthetic acidic amino acid, e.g., tetrazolyl derivatives of Gly and Ala. The aliphatic amino acids may be substituted by synthetic derivatives bearing non-natural aliphatic branched or linear side chains C$_n$H$_{2n+2}$ up to and including n=8.

More specifically, the present invention is directed to the following conotoxin peptides of general formula I:

| | |
|---|---|
| Mar1: | SEQ ID NO:2, wherein Xaa$_1$ is Tyr, Xaa$_2$ is Lys and Xaa$_3$ is hydroxy-Pro; |
| Mar2: | SEQ ID NO:3, wherein Xaa$_1$ is Tyr, Xaa$_2$ is Lys and Xaa$_3$ is hydroxy-Pro; |
| U036: | SEQ ID NO:4, wherein Xaa$_1$ is Tyr and Xaa$_3$ is hydroxy-Pro; |
| Q818: | SEQ ID NO:5, wherein Xaa$_1$ is Tyr, Xaa$_2$ is Lys and Xaa$_3$ is hydroxy-Pro; |
| Q819: | SEQ ID NO:6 wherein Xaa$_1$ is Tyr, Xaa$_3$ is hydroxy-Pro and Xaa$_4$ is Gln; |
| Q820: | SEQ ID NO:7 wherein Xaa$_2$ is Lys and Xaa$_3$ is hydroxy-Pro. |

Examples of synthetic aromatic amino acid include, but are not limited to, such as nitro-Phe, 4substituted-Phe wherein the substituent is C$_1$-C$_3$ alkyl, carboxyl, hyrdroxymethyl, sulphomethyl, halo, phenyl, —CHO, —CN, —SO$_3$H and —NHAc. Examples of synthetic hydroxy containing amino acid, include, but are not limited to, such as 4-hydroxymethyl-Phe, 4-hydroxyphenyl-Gly, 2,6-dimethyl-Tyr and 5-amino-Tyr. Examples of synthetic basic amino acids include, but are not limited to, N-1-(2-pyrazolinyl)-Arg, 2-(4-piperinyl)-Gly, 2-(4piperinyl)-Ala, 2-[3-(2S)pyrrolininyl]-Gly and 2-[3-(2S)pyrrolininyl]-Ala.

These and other synthetic basic amino acids, synthetic hydroxy containing amino acids or synthetic aromatic amino acids are described in Building Block Index, Version 3.0 (1999 Catalog, pages 4–47 for hydroxy containing amino acids and aromatic amino acids and pages 66–87 for basic amino acids; see also the website "amino-acids.com"), incorporated herein by reference, by and available from RSP Amino Acid Analogues, Inc., Worcester, Mass. Examples of synthetic acid amino acids include those derivatives bearing acidic functionality, including carboxyl, phosphate, sulfonate and synthetic tetrazolyl derivatives such as described by Ornstein et al. (1993) and in U.S. Pat. No. 5,331,001, each incorporated herein by reference.

Optionally, in the peptides of general formula I and the specific peptides described above, the Asn residues may be modified to contain an N-glycan and the Ser, Thr and Hyp residues may be modified to contain an O-glycan (e.g., g-N, g-S, g-T and g-Hyp). In accordance with the present invention, a glycan shall mean any N-, S- or O-linked mono-, di-, tri-, poly- or oligosaccharide that can be attached to any hydroxy, amino or thiol group of natural or modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified, e.g., with one or more O-sulfate, O-phosphate, O-acetyl or acidic groups, such as sialic acid, including combinations thereof. The glycan may also include similar polyhydroxy groups, such as D-penicillamine 2,5 and halogenated derivatives thereof or polypropylene glycol derivatives. The glycosidic linkage is beta and 1–4 or 1–3, preferably 1–3. The linkage between the glycan and the amino acid may be alpha or beta, preferably alpha and is 1.

Core O-glycans have been described by Van de Steen et al. (1998), incorporated herein by reference. Mucin type O-linked oligosaccharides are attached to Ser or Thr (or other hydroxylated residues of the present peptides) by a GalNAc residue. The monosaccharide building blocks and the linkage attached to this first GalNAc residue define the "core glycans," of which eight have been identified. The type of glycosidic linkage (orientation and connectivities) are defined for each core glycan. Suitable glycans and glycan analogs are described further in U.S. Ser. No. 09/420,797, filed 19 Oct. 1999 and in PCT Application No. PCT/US99/24380, filed 19 Oct. 1999 (PCT Published Application WO 00/23092), both incorporated herein by reference. A preferred glycan is Gal($\beta$1→3)GalNAc($\alpha$1→).

Optionally, in the peptides of general formula I and the specific peptides described above, pairs of Cys residues may be replaced pairwise with isoteric lactam or ester-thioether replacements, such as Ser/(Glu or Asp), Lys/(Glu or Asp) or Cys/Ala combinations. Sequential coupling by known methods (Barnay et al., 2000; Hruby et al., 1994; Bitan et al., 1997) allows replacement of native Cys bridges with lactam bridges. Thioether analogs may be readily synthesized using halo-Ala residues commercially available from RSP Amino Acid Analogues.

The present invention is also directed to the identification of the nucleic acid sequences encoding these peptides and their propeptides and the identication of nucleic acid sequence of additional related conotoxin peptides.

The present invention is further directed to a method of reducing/alleviating/decreasing the perception of pain by a subject or for inducing analgesia in a subject comprising administering to the subject an effective amount of the pharmaceutical composition comprising a therapeutically effective amount of a conotoxin peptide described herein or a pharmaceutically acceptable salt or solvate thereof. The present invention is also directed to a pharmaceutical composition comprising a therapeutically effective amount of a conotoxin peptide described herein or a pharmaceutically acceptable salt or solvate thereof and a pharmaceutically acceptable carrier.

Another embodiment of the invention contemplates a method of identifying compounds that mimic the analgesia activity of the instant peptide, comprising the steps of. (a) conducting a biological assay on a test compound to determine the analgesia activity; and (b) comparing the results obtained from the biological assay of the test compound to the results obtained from the biological assay of the peptide.

SUMMARY OF THE SEQUENCE LISTING

SEQ ID NO:1 is generic formula I for conotoxin peptides disclosed herein. SEQ ID NO:2 is a generic formula for the peptide Mar1. SEQ ID NO:3 is a generic formula for the peptide Mar2. SEQ ID NO:4 is a generic formula for the peptide U036. SEQ ID NO:5 is a generic formula for the peptide Q818. SEQ ID NO:6 is a generic formula for the peptide Q819. SEQ ID NO:7 is a generic formula for the peptide Q820. SEQ ID NO:8 is the nucleotide sequence of a degenerate primer for 3' RACE of the Mar1 gene. SEQ ID NO:9 is the nucleotide sequence of a degenerate primer for 5' RACE of the Mar 1 gene. SEQ ID NO:10 is the nucleotide sequence of a universal amplification primer. SEQ ID NO:11is a nucleotide sequence for the gene coding for the Mar1 propeptide. SEQ ID NO:12 is an amino acid sequence of the Mar1 propeptide. SEQ ID NO:13 is a nucleotide sequence for the gene coding for the Q818 propeptide. SEQ ID NO:14 is an amino acid sequence of the Q818 propeptide. SEQ ID NO:15 is a nucleotide sequence for the gene coding for the Q819 propeptide. SEQ ID NO:16 is an amino acid sequence of the Q819 propeptide. SEQ ID NO:17 is a nucleotide sequence for the gene coding for the Q820propeptide. SEQ ID NO:18 is an amino acid sequence of the Q820 propeptide. SEQ ID NO:19 is the nucleotide sequence of an amplification primer to isolate conotoxin peptides of the present invention. SEQ ID NO:20 is the nucleotide sequence of an amplification primer to isolate conotoxin peptides of the present invention.

DETAILED DESCRIPTION OF THE PREFERRED EMBODIMENT

The invention relates to relatively short conotoxin peptides, about 10–20 residues in length, which are naturally available in minute amounts in the venom of the cone snails or analogous to the naturally available peptides, and which preferably include two disulfide bonds. These conotoxin peptides have analgesic activity and are thus useful for treating or preventing pain.

The present invention, in another aspect, relates to a pharmaceutical composition comprising an effective amount of a conotoxin peptide described herein or a pharmaceutically acceptable salt or solvate thereof. Such a pharmaceutical composition has the capability of acting as analgesic agents.

The conotoxin peptides described herein are sufficiently small to be chemically synthesized. General chemical syntheses for preparing the foregoing conotoxin peptides are described hereinafter. Various ones of the conotoxin peptides can also be obtained by isolation and purification from specific Conus species using the technique described in U.S. Pat. No. 4,447,356 (Olivera et al., 1984), the disclosure of which is incorporated herein by reference.

Although the conotoxin peptides of the present invention can be obtained by purification from cone snails, because the amounts of conotoxin peptides obtainable from individual snails are very small, the desired substantially pure conotoxin peptides are best practically obtained in commercially valuable amounts by chemical synthesis using solid-phase strategy. For example, the yield from a single cone snail may be about 10 micrograms or less of conotoxin peptide. By "substantially pure" is meant that the peptide is present in the substantial absence of other biological molecules of the same type; it is preferably present in an amount of at least about 85% purity and preferably at least about 95% purity. Chemical synthesis of biologically active conotoxin peptides depends of course upon correct determination of the amino acid sequence.

The conotoxin peptides can also be produced by recombinant DNA techniques well known in the art. Such techniques are described by Sambrook et al. (1989). The peptides produced in this manner are isolated, reduced if necessary, and oxidized to form the correct disulfide bonds.

One method of forming disulfide bonds in the peptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. No. 3,842,067 (1974) and U.S. Pat. No. 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—$CH_2$-resin support, —NH BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in K. Horiki et al. (1978), using KF in DMF at about 60° C. for 24 hours with stirring, when a peptide having free acid at the C-terminus is to be synthesized. Following the coupling of the. BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):$CH_2Cl_2$ (1:1) or in DMF or $CH_2Cl_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above. The disulfide bonds in the conotoxin peptides described herein are preferably $Cys_1$-$Cys_4$ and $Cys_2$-$Cys_3$, which provides peptides with the greatest biological activity. However, peptides with $Cys_1$-$Cys_3$ and $Cys_2$-$Cys_4$ also have some biological activity.

The peptides are also synthesized using an automatic synthesizer. Amino acids are sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodimide in N-methylpyrrolidinone (NMP) or by 2-(1H-benzotriazole-1-yl)-1,1,3,3-tetrarnethyluronium hexafluorophosphate (HBTU) and diethylisopro-pylethylamine (DIEA). The FMOC protecting group is removed by treatment with a 20% solution of piperidine in dimethylformamide(DMF). Resins are subsequently washed with DMF (twice), followed by methanol and NMP.

On the basis of the amino acid sequence of Mar1, oligonucleotide primers are synthesized and used in 5' and 3' RACE (rapid amplification of cDNA ends) procedures to isolate the gene encoding the Mar 1 precursor protein. Alternatively, the DNA to be probed is DNA which is isolated and cloned in accordance with conventional techniques using general procedures well known in the art, such as described in Olivera et al. (1996). One example of a suitable degenerate primers are CAGGATCCAA(T/C) GGIGT(C/G/T)TG(T/C)TG(T/C)GG (SEQ ID NO:8) for 3" RACE and CTGGATCCGG(G/A)TG(A/G)CA(C/A/G)A (A/G)(C/T)TT(A/G)TAICC SEQ ID NO:9) for 5" RACE. As is common with conotoxin peptides, the identified DNAs coding for Mar1 codes for a precursor peptide which is translationally modified to yield the Mar1 peptide.

Additional conotoxin peptides are identified by cloning by reverse transcription-polymerase chain reaction (RT-PCR) from cone snail venom duct mRNA. The PCR primers are based on the DNA sequences coding for the precursor peptides described herein. RT-PCR of venom duct mRNA produces a product of about 250–300 nucleotides in Conus species that express conotoxin genes. The PCR product is then cloned into a plasmid vector and individual clones are sequenced to determine the sequence of various conotoxin genes. Alternatively, cDNA libraries are prepared from Conus venom duct using conventional techniques. DNA from single clones is amplified by conventional techniques using primers which correspond approximately to the M13 universal priming site and the M13 reverse universal priming site. Clones having a size of approximately 250 nucleotides are sequenced and screened for similarity in sequence to the propeptide described herein. In this manner, conotoxins having the basic structure and activity described herein are cloned from many Conus species.

Muteins, analogs or active fragments, of the foregoing conotoxin peptides are also contemplated here. See, e.g., Hammerland et al (1992). Derivative muteins, analogs or active fragments of the conotoxin peptides may be synthesized according to known techniques, including conservative amino acid substitutions, such as outlined in U.S. Pat. No. 5,545,723 (see particularly col. 2, line 50 to col. 3, line 8); U.S. Pat. No. 5,534,615 (see particularly col. 19, line 45 to col. 22, line 33); and U.S. Pat. No. 5,364,769 (see particularly col. 4, line 55 to col. 7, line 26), each incorporated herein by reference.

The conotoxin peptides of the present invention are useful for the treatment of pain or the induction of analgesia. As used herein the term "treating" also includes prophylaxis of pain in a patient or a subject having a tendency to develop such pain, and the amelioration or elimination or the developed pain once it has been established or alleviation of the characteristic symptoms of such pain. This invention envisions that the treatment of pain is most preferably the treatment of pain. As used herein the term "pain" shall refer to all types of pain. Preferably, the term refers to chronic pains, such as neuropathic pain, and post-operative pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post partum pain, migraine, angina pain, and genitourinary tract-related pain including cystitis, the term shall also preferredly refer to nociceptive pain or nociception.

Pharmaceutical compositions containing a compound of the present invention or its pharmaceutically acceptable salts or solvates as the active ingredient can be prepared according to conventional pharmaceutical compounding techniques. See, for example, *Remington's Pharmaceutical Sciences*, 18th Ed. (1990, Mack Publishing Co., Easton, Pa.). Typically, an analgesic amount of the active ingredient will be admixed with a pharmaceutically acceptable carrier. The carrier may take a wide variety of forms depending on the form of preparation desired for administration, e.g., intravenous, oral or parenteral. The compositions may further contain antioxidizing agents (e.g., to maintain disulfide bridges intact, including among others, lactate buffer and methionine), stabilizing agents, preservatives and the like.

"Pharmaceutical composition" means physically discrete coherent portions suitable for medical administration. "Pharmaceutical composition in dosage unit form" means physically discrete coherent units suitable for medical administration, each containing a daily dose or a multiple (up to four times) or a sub-multiple (down to a fortieth) of a daily dose of the active compound in association with a carrier and/or enclosed within an envelope. Whether the composition contains a daily dose, or for example, a half, a third or a quarter of a daily dose, will depend on whether the pharmaceutical composition is to be administered once or, for example, twice, three times or four times a day, respectively.

The term "salt", as used herein, denotes acidic and/or basic salts, formed with inorganic or organic acids and/or bases, preferably basic salts. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques.

Examples of such pharmaceutically acceptable salts include, but are not limited to, inorganic and organic addition salts, such as hydrochloride, sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alohatocopherol and the like; and the metal chelating agents such as citric acid, ethylenediamine tetraacetic acid (EDTA), sorbitol, tartaric acid, phosphoric acid and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, epidural, irrigation, intramuscular, release pumps, or infusion.

For example, administration of the active agent according to this invention may be achieved using any suitable delivery means, including:

(a) pump (see, e.g., Annals of Pharmacotherapy, 27:912 (1993); Cancer, 41:1270 (1993); Cancer Research, 44:1698 (1984));

(b) microencapsulation (see, e.g., U.S. Pat. Nos. 4,352,883; 4,353,888; and 5,084,350);

(c) continuous release polymer implants (see, e.g., U.S. Pat. No. 4,883,666);

(d) macroencapsulation (see, e.g., U.S. Pat. Nos. 5,284,761, 5,158,881, 4,976,859 and 4,968,733 and published PCT patent applications WO92/19195, WO 95/05452);

(e) naked or unencapsulated cell grafts to the CNS (see, e.g., U.S. Pat. Nos. 5,082,670 and 5,618,531);

(f) injection, either subcutaneously, intravenously, intra-arterially, intramuscularly, or to other suitable site; or (g) oral administration, in capsule, liquid, tablet, pill, or prolonged release formulation.

In one embodiment of this invention, an active agent is delivered directly into the CNS, preferably to the brain ventricles, brain parenchyma, the intrathecal space or other suitable CNS location, most preferably intrathecally.

Alternatively, targeting therapies may be used to deliver the active agent more specifically to certain types of cells, by the use of targeting systems such as antibodies or cell-specific ligands. Targeting may be desirable for a variety of reasons, e.g. if the agent is unacceptably toxic, if it would otherwise require too high a dosage, or if it would not otherwise be able to enter target cells.

The active agents, which are peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635. Suitable DNA sequences can be prepared synthetically for each active agent on the basis of the developed sequences and the known genetic code.

The active agent is preferably administered in an therapeutically effective amount. By a "therapeutically effective amount" or simply "effective amount" of an active compound is meant a sufficient amount of the compound to treat or alleviate pain or to induce analgesia at a reasonable benefit/risk ratio applicable to any medical treatment. The actual amount administered, and the rate and time-course of administration, will depend on the nature and severity of the condition being treated. Prescription of treatment, e.g. decisions on dosage, timing, etc., is within the responsibility of general practitioners or spealists, and typically takes account of the disorder to be treated, the condition of the individual patient, the site of delivery, the method of administration and other factors known to practitioners. Examples of techniques and protocols can be found in *Remington's Pharmaceutical Sciences*.

Dosage may be adjusted appropriately to achieve desired drug levels, locally or systemically. Typically the conopeptides of the present invention exhibit their effect at a dosage range from about 0.001 mg/kg to about 250 mg/kg, preferably from about 0.05 mg/kg to about 100 mg/kg of the active ingredient, more preferably from a bout 0.1 mg/kg to about 75 mg/kg, and most preferably from about 1.0 mg/kg to about 50 mg/kg. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved. In the event that the response in a subject is insufficient at such doses, even higher doses (or effective higher doses by a different, more localized delivery route) may be employed to the extent that patient tolerance permits. Continuous dosing over, for example 24 hours or multiple doses per day are contemplated to achieve appropriate systemic levels of compounds.

Advantageously, the compositions are formulated as dosage units, each unit being adapted to supply a fixed dose of active ingredients. Tablets, coated tablets, capsules, ampoules and suppositories are examples of dosage forms according to the invention.

It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician or veterinarian for use humans or animals.

The pharmaceutical compositions will generally contain from about 0.0001 to 99 wt. %, preferably about 0.001 to 50 wt. %, more preferably about 0.01 to 10 wt. % of the active ingredient by weight of the total composition. In addition to the active agent, the pharmaceutical compositions and medicaments can also contain other pharmaceutically active compounds. Examples of other pharmaceutically active compounds include, but are not limited to, analgesic agents, cytokines, conopeptides and other therapeutic agents useful in all of the major areas of clinical medicine. When used with other pharmaceutically active compounds, the conotoxin peptides of the present invention may be delivered in the form of drug cocktails. A cocktail is a mixture of any one of the compounds useful with this invention with another drug or agent. In this embodiment, a common administration vehicle (e.g., pill, tablet, implant, pump, injectable solution, etc.) would contain both the instant composition in combination supplementary potentiating agent. The individual drugs of the cocktail are each administered in therapeutically effective amounts. A therapeutically effective amount will be determined by the parameters described above; but, in any event, is that amount which establishes a level of the drugs in the area of body where the drugs are required for a period of time which is effective in attaining the desired effects.

As disclosed herein, the compounds and compositions of the present invention are useful in treating pain. As such, they may also be useful in treating inflammatory pain. Accordingly, the compounds and compositions of the present invention may also be utilized to treat numerous inflammatory disease states and disorders other than pain. For example, the compositions and compounds may be useful for treating disorders or diseases including but not limited to: Alzheimer's disease, multiple sclerosis, attenuation of morphine withdrawal, cardiovascular changes, oedema, such as oedema caused by thermal injury, chronic inflammatory diseases such as rheumatoid arthritis, asthma/ bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detrusor hyperreflexia, demyelinating diseases such as multiple sclerosis and amyotrophic lateral sclerosis, asthmatic disease, small cell carcinomas, in particular small cell lung cancer, depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosis conjunctivitis, vernal conjunctivitis, contact dermatitis, atopic dermatitis, urticaria, and other eczematoid dermatitis and emesis; central nervous system disorders such as anxiety, depression, psychosis and schizophrenia; neurodegenerative disorders such as AIDS related dementia, senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, inflammatory diseases such as inflammatory bowel disease, irritable bowel syndrome, psoriasis, fibrositis, ocular inflammation, osteoarthritis and rheumatoid arthritis; allergies such as eczema and rhinitis; hypersensitivity disorders such as poison ivy; ophthalmic diseases such as conjunctivitis, vernal conjunctivitis, dry eye syndrome, and the like; cutaneous diseases such as contact dermatitis, atopic dermatitis, urticaria, and other eczematoid dermatitis; oedema, such as oedema caused by thermal injury; addiction disorders such as alcoholism; stress related somatic disorders; reflex sympathetic dystrophy such as shoulder/hand syndrome; dysthymic disorders; neuropathy, such as diabetic or peripheral neuropathy and chemotherapy-induced nemopathy; postherpetic and other neuralgias; asthma; osteoarthritis; rheumatoid arthritis; migraine reperfusion injury to an ischemic organ, e.g., reperfusion injury to the ischemic myocardium, myocardial infarction, inflammatory bowel disease, rheumatoid arthritis, osteoarthritis, hypertension, psoriasis, organ transplant rejections, organ preservation, impotence, radiation-induced injury, asthma, atherosclerosis, thrombosis, platelet aggregation, metastasis, influenza, stroke, burns, trauma, acute pancreatitis, pyelonephritis, hepatitis, autoimmune diseases, insulin-dependent diabetes mellitus, disseminated intravascular coagulation, fatty embolism, adult and infantile respiratory diseases, carcinogenesis and hemorrhages among many others.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982; Sambrook et al., 1989; Ausubel et al., 1992; Glover, 1985; Anand, 1992; Guthrie and Fink, 1991; Harlow and Lane, 1988; Jakoby and Pastan, 1979*; Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); Riott, *Essential Immunology*, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986).

EXAMPLES

The present invention is described by reference to the following Examples, which are offered by way of illustration and are not intended to limit the invention in any manner. Standard techniques well known in the art or the techniques specifically described below were utilized.

Example 1

Isolation of Mar1 Conotoxin

The venom of *Conus marmoreus* was obtained from snails collected in the Philippines. The venom was lyophilized and stored at −70° C. until use. Crude venom was extracted using previously described methods (McIntosh et al., 1984). Reverse phase HPLC purification was accomplished with an analytical (4.6 mm i.d.×25 cm) Vydac $C_{18}$ column. Column pore size was 300 Å. Crude venom extract was size-fractionated using a column (2.54 cm diam×188 cm length) packed with Sephadex G-25 (dry bead diameter 20–80 $\mu$m). Elution buffer was 1.1% acetic acid at 4° C. Flow rate was ~18.3 ml/h. Fractions 66–77, those fractions eluting in a range corresponding to small peptides, were further purified. Throughout subsequent purification, HPLC fractions were assayed by means of intracerebral ventricular (i.c.v.) injection into mice (Clark et al., 1981). I.c.v. injection of fractions containing Mar1 produced hypokinetic "sluggish" symptoms.

These fractions were combined, lyophilized and resuspended in 0.1% trifluoroacetic acid and purified on a Vydak C-18 column using a linear 1% buffer B/min gradient where buffer A is 0.1% trifluoroacetic acid and buffer B is 0.092% trifluoroacetic acid, 60% acetonitrile. The gradient began at 10% buffer B. The material in the fraction which eluted around 30 minutes was lyophilized and resuspended in 0.05% heptafluorobutyric acid (HFBA). It was then purified on a Vydak C-18 column using a linear 1% buffer B/min gradient where buffer A is 0.05% HFBA and buffer B is 0.05% HFBA, 60% acetonitrile. The gradient began at 30% buffer B. The material in the fraction which eluted around 18 minutes was lyophilized and dissolved in 10 mM $NaH_2PO_4$, 50% $CH_3CN$ pH 2.5 (buffer A). The material was then purified using a Vydak protein SCX column (0.75×5 cm) using a linear 1% B/min gradient where buffer B is the same as buffer A, but with the addition of 250 mM NaCl. Flow rate was 1 ml/min for the last three purifications. Absorbance was monitored at 233 nm, 214 nm, 214 nm and 220 run in the four purification steps, respectively. The final fraction was then desalted using reverse phase HPLC.

The peptides Mar2 and U036 were similarly obtained. Additional conotoxin peptides of the class of conotoxins represented by Mar1 are obtained similarly from other species, including, but not limited to, *C. bandanus, C. striatus, C. textile, C. pennaceus, C. nussatella, C. arenatus,*

*C. tesselatus, C. generalis, C. flavidus, C. rattus, C. parvatus, C. ventricosus, C. purpurascens,* and *C. strombus.*

Example 2

Mar1 Conopeptide Analysis

The peptide isolated in Example 1 was reduced and cysteines were carboxymythelated as previously described (Gray et al. 1981). The alkylated peptide was purified with a Vydac $C_{18}$, analytical column using a linear gradient of 0.1% trifluoracetic acid and 0.092% trifluoroacetic acid in 60% acetonitrile. Alkylated peptide was sequenced by Edman degradation and yielded NGVCCGYKLCHOC (SEQ ID NO:2) where O is 4-trans hydroxyproline.

Electrospray ionization mass spectra were measured using a Micromass Quattro II Triple Quadrupole Mass Spectrometer with Micromass MassLynx operating system. The samples (~100 pmoles) were resuspended in 0.1 ml of 50% acetonitrile with 0.05% TFA and automatically infused with a flow rate of 0.05 ml/min in the same solvent system. The instrument was scanned over the m/z range 50–2,000 with a capillary voltage of 2.95 kVolts and a cone voltage of 64 Volts. The resulting data were analyzed using MassLynx software. Mass spectrometry of the peptide verified the sequence, indicated that Cys residues are present as disulfides and the C-terminus is the free carboxyl [monoisotopic $MH^+$ (Da): calculated, 1408.5; observed 1408.5].

Example 3

Synthesis of Mar1 Conopeptide

Peptides were synthesized on a RINK amide resin using FMOC (N-(9-fluorenyl)methoxycarboxyl) chemistry and standard side chain protection except on cysteine residues. Cys residues were protected in pairs with either S-trityl or S-acetamidomethyl (acm).groups. All three possible disulfide forms of the peptide were synthesized. The peptides were removed from the resin, precipitated and a two-step oxidation protocol was used to selectively fold the peptides as previously described (Walker et al. 1999).

Mar1 has four Cys residues and therefore three possible disulfide arrangements. All three disulfide bond arrangements were synthesized in order to unequivocally identify the native configuration. Peptides were initially synthesized in linear form using pairwise protection of Cys residues. FeCN oxidation was used to remove trityl protecting groups and close the first disulfide bridge. Iodine oxidation was subsequently used to remove ACM protection groups and close the second bridge. Using this method, each possible disulfide arrangement was synthesized, i.e., [Cys1-Cys2, Cys3-Cys4]; [Cys1-Cys3, Cys2-Cys4]; and [Cys1-Cys4, Cys2-Cys3]. Synthesis of each isomer was confirmed with mass spectrometry [calculated monoisotopic $MH^+$ 1408.5; observed: 1408.6, 1408.7 and 1408.6, respectively].

The three forms of the peptide were distinguishable using reverse phase HPLC based on elution time. In addition, they were distinguishable by peak width, with the [Cys1-Cys4, Cys2-Cys3] form having the narrowest peak width. Specifically, ~200 pmol each of the three possible disulfide forms of synthetic Mar1 were chromatographed using reverse phase HPLC and compared with native Mar1. The disulfide connectivities are: 1, [Cys1-Cys3, Cys2-Cys4]; 2, [Cys1-Cys4, Cys2-Cys3]; 3, [Cys1-Cys2, Cys3-Cys4]. In all HPLC runs, buffer A=0.1% trifluoracetic acid and buffer B=0.092% trifluoracetic acid, 60% acetonitrile. The gradient began at 15% B and increased 1% B/min. The column was an analytical C-18. Flow rate was 1 ml/min. Absorbance was monitored at 220 nm. Both the native peptide's elution time and peak shape both match that of the [Cys1-Cys4, Cys2-Cys3] disulfide form. Additionally , co-injection of native peptide with each of the synthetic forms indicates that Mar1 co-elutes with and only with the [Cys1-Cys4, Cys2-Cys3] configuration unambiguously identifying this disulfide arrangement as native.

Other peptides, namely Mar2 Q818, Q819, Q820, and U036 are similarly purified and sequenced. The results indicate that they belong to the same class of peptides as defined by the Mar1 conopeptide.

The position of cysteine residues is remarkably consistent, being identical for all investigated peptides of this class. Without departing from the preferred embodiment it is clear that instant cysteine residues can be L or D isomers. Alternatively they can be replaced with L or D homocysteine. Furthermore, disulphide bridges can be replaced with isosteric lactam, ester, thioether or thioester replacements, see for example U.S. Pat. Nos. 5,942,599; 5,883,293; 3,980,631; 4,316,890, incorporated herein by way of reference. Bridges of this nature can be synthesized readily by replacement of Cys-Cys pairs with Lys-Glu, Ser-Glu or Cys-Ala or Cys-Glu respectively. Thioether analogs maybe readily synthesized using halo-Ala residues (commercially available from RSP Amino Acid analogues). Within the constraints of the peptide conformation described above, as well as considerations of the biological effects of such functionalities, it will be appreciated by those of skill in the art that a peptide mimic may serve equally well as a peptide for the purpose of providing the specific conformation required for folding instant peptides and eliciting appropriate biological responses. Accordingly, it is contemplated as being within the scope of the present invention to produce Mar analogs having the above-described conformational features through the use of naturally-occurring amino acids, amino acid derivatives, analogs or non-amino acid molecules capable of being joined to form the appropriate conformation. A non-peptide analog, or an analog comprising peptide and non-peptide components, is sometimes referred to herein as a "peptidomimetic," or sometimes as an "isosteric peptidomimetic" to designate substitutions or derivations of peptide-based analogs that possess the same conformational features and/of other functionalities (Blondelle et al., 1995). As used herein, a "peptidomimetic" is a compound that can imitate (agonist) or block (antagonist) the biological effect of a peptide. The following factors should be considered to achieve the best possible agonist peptidomimetic a) metabolic stability, b) good bioavailability, c) high receptor affinity and receptor selectivity, and d) minimal side effects. The use of isosteric peptidomimetics for the development of high-affinity and/or selective peptide analogs is well known in the art.

Example 4

Isolation of cDNA Encoding Conotoxin Mar1

Based on the amino acid sequence of the Mar1 peptide, degenerate oligonucleotide primers were synthesized and used in 5' and 3' RACE (rapid amplification of cDNA ends) procedures to isolate the gene encoding the Mar1 precursor protein. For 3' RACE, the Mar1F primer was synthesized with the sequence CAGGATCCAA(T/C)GGIGT(C/G/T)TG (T/C)TG(T/C)GG (SEQ ID NO:8) corresponding to the amino acids NGVCCG (residues 1–6 of SEQ ID NO:2) of the Mar 1 conotoxin. For 5' RACE, the Mar1R reverse primer was synthesized with the sequence CTGGATCCGG (G/A)TG(A/G)CA(C/A/G)A(A/G)(C/T)TT(A/G)TAICC (SEQ ID NO:9) corresponding to the amino acids GYKLCHP (residues 6–12 of SEQ ID NO:2) of the Mar1 conotoxin. Each of these oligonucleotides includes a synthetic recognition site for the restriction enzyme BamHI at the 5' end to facilitate cloning of the PCR products. *Conus marmoreus* mRNA was isolated and used to synthesize cDNA with adapter sequences appended to the 5' and 3' termini. The adapter sequences contain a region complementary to a universal amplification primer (Lib-U primer; AAGCTCGAGTAACAACGCAGAGT (SEQ ID NO:10)). The Lib-U primer contains a XhoI site to facilitate cloning of the PCR products. 3' RACE amplification of the *C. marmoreus* cDNA with the Mar1 F and Lib-U primers generated a specific 620 bp PCR product, and 5' RACE with the Mar1Rand Lib-U primers generated a 310 bp PCR product. Each of these PCR products was directionally cloned into the BamHI and XhoI sites of the plasmid vector pBluescript II SK⁻. Plasmid clones containing inserts of the appropriate size were identified and DNA sequences were determined for several of the 5' RACE and 3' RACE clones. All of the 5' RACE and 3' RACE clones corresponded to the Mar1 sequence. The Mar1F and Mar1R primers were designed to generate overlapping cDNA fragments, and by aligning the 5' RACE and 3' RACE sequences the complete Mar1 gene sequence was deduced.

The Mar1 cDNA sequence is 790 bp, followed by a poly A tail at the 3' end. The first open reading frame encountered from the 5' end of the cDNA initiates from a start codon at base pair 82, and encodes a protein of 61 amino acids. The Mar1 conotoxin sequence resides at the C-terminus of this precursor protein, and is immediately preceded by a basic arginine residue. The first 24 amino acids of the precursor protein comprise a highly hydrophobic signal sequence. Each of these features is characteristic of conotoxin precursor protein structure. Following the stop codon, there is 522 bp of 3' untranslated region sequence.

The DNA sequence of the signal sequence region and the 3' untranslated region are used to design PCR primers to isolate conotoxin genes related to this novel Mar1 peptide from other Conus species. The Mar1 coding sequence (SEQ ID NO:11) and the Mar1 propeptide sequence (SEQ ID NO:12) are set forth in Table 1.

TABLE 1

DNA Sequence (SEQ ID NO:11) and
Protein Sequence (SEQ ID NO:12) of Mar1

```
ggcgaataca  cctggcaggt  actcaacgaa  cttcaggaca  cattcttttc  acctggacac tggaaactga  caacaggcag  a atg cgc tgt ctc cca gtc ttg atc att ctt
                         Met Arg Cys Leu Pro Val Leu Ile Ile Leu ctg ctg ctg act gca tct gca cct ggc gtt gtt gtc cta ccg aag acc
Leu Leu Leu Thr Ala Ser Ala Pro Gly Val Val Val Leu Pro Lys Thr gaa gat gat gtg ccc atg tca tct gtc tac ggt aat gga aag agt atc
Glu Asp Asp Val Pro Met Ser Ser Val Tyr Gly Asn Gly Lys Ser Ile cta cga gga att ctg agg aac ggt gtt tgc tgt ggc tat aag ttg tgc
Leu Arg Gly Ile Leu Arg Asn Gly Val Cys Cys Gly Tyr Lys Leu Cys cat cca tgt taaccagcat gaagggaaat gactttggat gagacccctg
His Pro Cys cgaactgtcc  ctggatgtga  aatttggaaa  gcagactgtt  cctttcgcac  gtattcgtgg aatttcgaat  ggtcgtaaac  aacacgctgc  cacttgcagg  ctactatctc  tctgtccttt catctgtgga  aatggatgat  ctaacaactg  aaatatcaga  aattttttcaa tggctataca ctatgaccat  gtagtcagta  attatatcat  ttggaccttt  tgaaatattt  ttcaatatgt aaagtttttg  caccctggaa  aggtcttttg  gagttaaata  ttttagtatg  ttatgttttg catacaagtt  atagaatgct  gtctttcttt  ttgttcccac  atcaatggtg  ggggcagaaa ttatttgttt  tggtcaatgt  aattatgacc  tgcatttagt  gctatagtga  ttgcattttc agcgtggaat  gtttaatctg  caaacagaaa  gtggttgatc  gactaataaa  gatttgcatg gcacaaaaaa  aaaaaaaaa a
```

Conus peptides are initially translated from mRNA as prepropeptide precursors that are subsequently processed into the small mature neuroactive toxins. Conopeptides can be grouped into superfamilies, based on the signal sequences of the precursors and on the disulfide framework of the mature toxin. Thus, in the "O" superfamily for example there are: (ω-conotoxins (Ca⁺⁺ channel antagonists), μO-conotoxins (Na⁺ channel blockers), δ-conotoxins (peptides that delay inactivation of Na⁺ channels) and κ-conotoxins (K⁺ channel blockers). Peptides in these four families share a highly conserved signal sequence as well as the same disulfide framework. Thus, the polypeptides belonging to the same superfamily can be processed to mature conotoxins which are biochemically and pharmacologically diverse.

Analysis of a cDNA clone of Mar1 indicates clearly that this peptide is a member of the T-superfamily. In members of the O-superfamily, although there is hypermutation of toxin sequences, the disulfide connectivity is conserved. In contrast, the previously identified T-superfamily conotoxins vs. Mar1 have both a divergent arrangement of Cys residues, and most surprisingly, a different disulfide bond linkage. This is the first known example of such a divergent disulfide connectivity within members of a Conus peptide superfamily. Thus, the Mar1 peptide defines a distinct branch of the T-conopeptide superfamily clearly different from T-superfamily peptides previously characterized.

While Mar1 precursor exhibits significant sequence homology to a previously identified family of conotoxin genes, the T-superfamily, the mature Mar1 peptide is totally distinct from any of the previously isolated T-superfamily conotoxins. Previously isolated T-superfamily conotoxins all share the cysteine framework —CC—CC— (Walker et al., 1999). The position of the cysteine residues within the conotoxin sequence determines the disulphide linkages, and therefore the tertiary structure of the peptide. These disulphide linkages result in the formation of 'loops' of peptide sequence, and the peptide toxins can be classified according to the number of loops that they contain. One example is the 2-loop structure: cc . . . (1) . . . c . . . (2) . . . c. Examples of this structure are the α-conotoxins (*C. geographus, C. striatus*). A second example is the 3-loop structure: cc . . . (1) . . . c . . . (2) . . . . c . . . (3) . . . c. Examples of this structure are μ-conotoxins (*C. geographus, C. textile*, Scratcher Peptide). A third example is the 4-loop structure: c . . . (1) . . . c . . . (2) . . . cc . . . (3) . . . c . . . (4) . . . c. Examples of this structure are ω-conotoxins (*C. geographus, C. magus, C. textile*, the King-Kong peptide). The latter structure is the most common having been identified in over 20 conotoxin peptides.

The cysteine framework of the Mar1 conotoxin is similar to that of the α-conotoxins, a large family of nicotinic receptor antagonists, yet the sequence alignment of the prepropeptides clearly indicates that Mar1 and α-conotoxins are derived from completely unrelated precursors. The occurrence of the Mar1 conotoxin within the T-superfamily provides a demonstration of the ability of Conus species to evolve novel toxin peptide frameworks within the same conotoxin superfamily.

Like many Conus peptides, Mar1 is rich in disulfides, with four of thirteen residues being Cys residues. Two other groups of Conus peptides were previously shown to have four Cys residues, the α-conotoxins and T-superfamily conotoxins (McIntosh et al., 1999). All α-conotoxins and T-superfamily conotoxins characterized to date have [Cys1-Cys3, Cys2-Cys4] connectivity. In contrast, Mar1 has [Cys1-Cys4, Cys2-Cys3] connectivity, a pattern unprecedented among Conus peptides. In addition to the novel disulfide bond connectivity, Mar1 bears little if any sequence similarity to the (α-Conotoxins or other T-superfamily peptides, and clearly represents a new class of Conus peptide.

Example 5

Isolation of DNA Encoding Same Class of Conotoxins

The DNA sequence of the signal sequence region and the 3' untranslated region can be used to design PCR primers to isolate conotoxin genes related to this novel Mar 1 peptide from other Conus species. A pair of such PCR primers was synthesized:

TOOG17 forward primer (GGAATTCGGAAGCTGACTACAAGC; SEQ ID NO:19) and

MarSR reverse primer (CTGGATCCTTCATGCTGGTFAA; SEQ ID NO:20).

Reverse trancription-PCR of venom duct RNA will yield a PCR product of 200 bp in Conus species that express Mar-related conopeptides. RT-PCR with the TOOG17+ MarSR primers was used to isolate Mar1-related conopeptide genes from *C. bandanus* (Q818), *C. textile* (Q819) and *C. pennaceus* (Q820). These novel genes share significant homology with the original Mar1 conopeptide, both in the precursor and mature toxin regions. The Q818 coding sequence (SEQ ID NO:13) and the Q818 propeptide sequence (SEQ ID NO:14) are set forth in Table 2. The Q819 coding sequence (SEQ ID NO:15) and the Q819 propeptide sequence (SEQ ID NO:16) are set forth in Table 3. The Q820 coding sequence (SEQ ID NO:17) and the Q820 propeptide sequence (SEQ ID NO:18) are set forth in Table 4.

TABLE 2

DNA Sequence (SEQ ID NO:13) and
Protein Sequence (SEQ ID NO:14) of Q818

```
atg cgc tgt ctc cca gtc ttg atc att ctt ctg ctg ctg act gca tct
Met Arg Cys Leu Pro Val Leu Ile Ile Leu Leu Leu Leu Thr Ala Ser gca cct ggc gtt gat gtc cta ccg aag acc gaa gat gat gtg ccc ctg
Ala Pro Gly Val Asp Val Leu Pro Lys Thr Glu Asp Asp Val Pro Leu tca tct gtc tac gat aat aca aag agt atc cta cga gga ctt ctg gac
Ser Ser Val Tyr Asp Asn Thr Lys Ser Ile Leu Arg Gly Leu Leu Asp aaa cgt gct tgc tgt ggc tac aag ctt tgc tca cca tgt taaccagcat
Lys Arg Ala Cys Cys Gly Tyr Lys Leu Cys Ser Pro Cys gaaggatcc
```

TABLE 3

DNA Sequence (SEQ ID NO:15) and
Protein Sequence (SEQ ID NO:16) of Q819

```
atg cac tgt ctc cca atc ttc gtc att ctt ctg ctg ctg act gca tct
Met His Cys Leu Pro Ile Phe Val Ile Leu Leu Leu Leu Thr Ala Ser
```

TABLE 3-continued

| DNA Sequence (SEQ ID NO:15) and Protein Sequence (SEQ ID NO:16) of Q819 |
|---|
| gga cct agc gtt gat gcc caa ctg aag acc aaa gat gat gtg ccc ctg<br>Gly Pro Ser Val Asp Ala Gln Leu Lys Thr Lys Asp Asp Val Pro Leu |
| tca tct ttc cga gat cat gca aag agt acc cta cga aga ctt cag gac<br>Ser Ser Phe Arg Asp His Ala Lys Ser Thr Leu Arg Arg Leu Gln Asp |
| aaa cag act tgc tgt ggc tat agg atg tgt gtt cct tgt ggt<br>Lys Gln Thr Cys Cys Gly Tyr Arg Met Cys Val Pro Cys Gly |
| taaccagcat gaaggatcc |

TABLE 4

| DNA Sequence (SEQ ID NO: 17) and Protein Sequence (SEQ ID NO: 18) of Q820 |
|---|
| atg cgc tgt ctc cca gtc ttc gtc att ctt ctg ctg ctg act gca tct<br>Met Arg Cys Leu Pro Val Phe Val Ile Leu Leu Leu Leu Thr Ala Ser |
| gca cct agc gtt gat gcc aaa gtt cat ctg aag acc aaa ggt gat ggg<br>Ala Pro Ser Val Asp Ala Lys Val His Leu Lys Thr Lys Gly Asp Gly |
| ccc ctg tca tct ttc cga gat aat gca aag agt acc cta caa aga ctt<br>Pro Leu Ser Ser Phe Arg Asp Asn Ala Lys Ser Thr Leu Gln Arg Leu |
| cag gac aaa agc act tgc tgt ggc ttt aag atg tgt att cct tgt<br>Gln Asp Lys Ser Thr Cys Cys Gly Phe Lys Met Cys Ile Pro Cys |
| cgttaaccag catgaaggat cc |

Other related peptides of the same class are isolated in a similar manner from other Conus species, including, but not limited to, *C. bandanus, C. striatus, C. textile, C. pennaceus, C. nussatella, C. arenatus, C. tesselatus, C. generalis, C. flavidus, C. rattus, C. parvatus, C. ventricosus, C. purpurascens* and *C. strombus*. Alternatively, cDNA libraries are prepared from Conus venom duct using conventional techniques. DNA from single clones is amplified by conventional techniques using primers which correspond approximately to the M13 universal priming site and the M13 reverse universal priming site. Clones having a size of approximately 250–300 nucleotides are sequenced and screened for similarity in sequence to Mar1. In this manner, additional related conotoxins are cloned from many Conus species, such as those listed above.

Example 6

Analgesic Activity of Mar1

Adult male CF-1 mice (25–35 g) were used for all experiments. Mice were housed five per cage, maintained on a 12 hr light/dark cycle and allowed free access to food and water; Analgesic activity was assessed by placing mice in a plexiglass cylinder (10.2 cm diam×30.5 cm high) on a hot plate (Mirak model HP72935, Barnstead/Thermolyne, Dubuque, Iowa) maintained at 55° C. Thirty minutes before the hot-plate test, animals were treated with a dose of Mar 1 or vehicle (0.9% saline) by freehand intrathecal (i.t.) injection in a volume of 5 $\mu$l essentially as described by others (Hylden and Wilcox, 1980). The time from being placed on the plate until each mouse either licked its hind paws or jumped was recorded with a stopwatch by a trained observer unaware of the treatments. An arbitrary cut-off time of 60 s was adopted to minimize tissue injury. Hot-plate test data were analyzed by ANOVA followed by Dunnett's test for multiple comparison with $P<0.05$ considered significant. Statistical analysis was performed with GraphPad Prism software (San Diego, Calif.). Shortly after the hot-plate test, mice were placed on a 3 cm diameter rotarod turning at 6 rpm (model 7650, Ugo Basile, Comerio, Italy). Mice were considered impaired if they fell three times in 1 min.

Native peptide (2 nmol) injected intrathecally into three mice produced a latency to first hind paw lick (a nociceptive response) of 39.5±13.5 s, suggestive of potent analgesic activity. The activity of the native material purified from live animals was similar to that of synthetic peptide. Intrathecal administration of synthetic Mar1 produced a dose-dependent (0.1 to 10 nmol, i.t.) increase in the latency to first hind paw lick [$P<0.01$] in the hot plate test. At doses of 1 and 10 nmol i.t., Mar1 significantly increased the latency to lick the hind paw in this test. Similar potent analgesic activity is observed with other native and synthetic Mar-like conopeptides of the invention.

Motor impairment was assessed in all injected mice by means of a rotarod test. Motor impairment was not seen in any mouse injected either intrathecally or intraperitoneally. Injection of high doses of Mar1 (25 mnol) by i.c.v. administration resulted in akinesia and seizures in two mice tested. Thus, Mar1 and related Mar-like conopeptides are potent analgesics when tested in a mouse hot plate assay at intrathecal doses and do not produce gross motor impairment or impair performance on the rotarod test.

Additional conopeptides are prepared which display analgesic activity. These peptides contain residues that are synthetic aromatic, aliphatic, and basic amino acid residues as previously described. Such peptides are then synthesized as described supra and screened in mice assay to identify among them those that display activity similar to originally discovered Mar1 peptide.

Example 7

Analgesic Activity of Mar1

Analgesic activity of Mar1 is also tested in a persistent pain models as follows.

Persistent pain (formalin test). Intrathecal (it) drug injections were performed as described by Hylden and Wilcox (1980). Mar1, Mar2 or vehicle was administered in a volume of 5 µl. Fifteen minutes after the it injection, the right hindpaw was injected with 20 µl of 5% formalin. Animals were placed in clear plexiglass cylinders backed by mirrors to facilitate observation. Animals were closely observed for 2 minutes per 5 minute period, and the amount of time the animal spent licking the injected paw was recorded in this manner for a total of 45–50 minutes. Results were expressed as licking time in seconds per five minutes. At the end of the experiment, all animals were placed on an accelerating rotorod and the latency to first fall was recorded. Mar1 is found to be active in this model.

Example 7

Analgesic Activity of Mar1

Analgesic activity of Mar1 and Mar 2 are also tested in an acute pain models as follows.

Acute pain (tail-flick). Mar1 or saline is administered intrathecally (i.t.) according to the method of Hylden and Wilcox (1980) in a constant volume of 5 µl. Mice are gently wrapped in a towel with the tail exposed. At various timepoints following the i.t. injection, the tail is dipped in a water bath maintained at 54° C. and the time to a vigorous tail withdrawal is recorded. If there is no withdrawal by 8 seconds, the tail is removed to avoid tissue damage. Mar1 is found to be active in this model.

The data obtained demonstrate that Mar1 has potent analgesic properties in two commonly used models of pain: acute and persistent pain models. Mar1 administered intrathecally reduced the response latency in the tail flick model of acute pain, and is effective in the low nanomole range.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Barnay, G. et al. (2000). *J. Med Chem.*
Bitan, G. et al. (1997). *J. Peptide Res.* 49:421–426.
Blondelle et al. (1 995). *Trends in Analytical Chem.* 14:83–92.
Blount, K. et al. (1992). *Toxicon* 30:835–842.
Bodansky et al. (1966). *Chem. Ind.* 38:1597–98.
Cartier, G. E. et al. (1996). *J. Biol. Chem.* 271:7522–7528.
Chaplan, S. R. et al. (1994). *J. Neurosci. Methods* 53:55–63.
Clark, C. et al. (1981). *Toxicon* 19:691–699.
Craig, A. G. et al. (1999). *J. Biol. Chem.* 274:13752–13759.
Cruz, L. J. at al. (1976). *Verliger* 18:302–308.
Cruz, L. J. et al. (1987). *J. Biol. Chem.* 260:9280–9288.
Fainzilber, M. et al. (1994). *Biochemistry* 33:9523–9529.
Gray, W. R. et al. (1981). *J. Biol. Chem.* 256:4734–4740.
Haack, J. A. et al. (1990). *J. Biol. Chem.* 265:60254029.
Hammerland et al. (1992). *Eur. J. Pharmacol.* 226:239–244.
Heading, C. (1999). *Curr. Opin. CPNS Invest. Drugs* 1:153–166
Hubry, V. et al. (1994). *Reactive Polymers* 22:231–241.
Hylden, J. L. K. and Wilcox, G. (1980). *Eur. J. Pharmacol.* 67:313–316.
Horiki, K. et al. (I978). *Chemistry Letters* 165–68.
Jacobsen, R. et al. (1997). *J. Biol. Chem.* 272:22531–22537.
Johnson, D. S. et al. (1995). *Mol. Pharmacol.* 48:194–199.
Kapoor (1970). *J. Pharm. Sci.* 59:1–27.
Kornreich, W. D. et al. (1986). U.S. Pat. No. 4,569,967.
Luo, S. et al. (1998). *J. Neurosci.* 18:8571–8679.
Malmberg, A. B et al. (1998). *Pain* 76:215–222.
Marshall, I. G. and Harvey, A. L. (1990). *Toxicon* 28:231–234.
Martinez, J. S. et al. (1995). *Biochem.* 34:14519–14526.
McIntosh, J. M. et al. (1982). *Arch. Biochem. Biophys.* 218:329–334.
McIntosh, J. M. et al. (1984). *J. Biol. Chem.* 259:14343–14346.
McIntosh, J. M. et al. (1995). *J. Biol. Chem.* 270:16796–16802.
McIntosh, J. M. et al. (1998). *Methods Enzymol.* 294:605–624.
McIntosh, J. M. et al. (1999). *Annu. Rev. Biochem.* 68:59–88.
Mena, E. E. et al. (1 990). *Neurosci. Lett.* 118:241–244.
*The Merck Manual of Diagnosis and Therapy*, 16th Ed. (Merck Research Laboratories., Rahway, N.J., 1992).
Methoden der Organischen Chemie (Houben-Weyl): *Synthese von Peptiden*, E. Wunsch (Ed.), Georg Thieme Verlag, Stuttgart, Ger. (1974).
Myers, R. A. et al. (1991). *Biochemistry* 30:9370–9377.
Nishiuchi, Y. et al. (1993). *Int. J. Pept. Protein Res.* 42:533–538.
Nowak, L. et al. (1984). *Nature* 307:462–465.
Olivera, B. M. et al. (1984). U.S. Pat. No. 4,447,356.
Olivera, B. M. et al. (1985). *Science* 230:1338–1343.
Olivera, B. M. et al. (1996). U.S. Pat. No. 5,514,774.
Ornstein, et al. (1993). *Biorganic Medicinal Chemistry Letters* 3:43–48.
*Remington's Pharmaceutical Sciences*, 18th Ed. (1990, Mack Publishing Co., Easton, Pa.).
Rivier, J. R. et al. (1978). *Biopolymers* 17:1927–38.
Rivier, J. R. et al. (1987). *Biochem.* 26:8508–8512.
Sambrook, J. et al. (1989). *Molecular Cloning: A Laboratory Manual*, 2nd Ed., Cold Spring Harbor Laboratory, Cold Spring Harbor, N.Y.
Schroder & Lubke (1965). *The Peptides* 1:72–75, Academic Press, NY.
Shon, K.-J. et al. (1994). *Biochemistry* 33:11420–11425.
Stewart and Young, *Solid-Phase Peptide Synthesis*, Freeman & Co., San Francisco, Calif. (1969).
Vale et al. (1978). U.S. Pat. No. 4,105,603.
Van de Steen, P. et al. (1998). *Critical Rev. in Biochem. and Mol. Biol.* 33:151–208.
Walker, C. et al. (1999). *J. Biol. Chem.* 274:30664–30671.
Zafaralla, G. C. et al. (1988). *Biochemistry* 27:7102–7105.
Zhou L. M., et al. (1996). *J. Neurochem.* 66:620–628.
U.S. Pat. No. 3,972,859.
U.S. Pat. No. 3,980,631.
U.S. Pat. No. 3,842,067.
U.S. Pat. No. 3,862,925.
U.S. Pat. No. 4,316,890.
U.S. Pat. No. 5,331,001.
U.S. Pat. No. 5,364,769.
U.S. Pat. No. 5,550,050.
U.S. Pat. No. 5,534,615.
U.S. Pat. No. 5,545,723.
U.S. Pat. No. 5,859,186.

U.S. Pat. No. 5,883,293.
U.S. Pat. No. 5,942,599.
PCT Published Application WO 92/19195.
PCT Published Application WO 94/25503.
PCT Published Application WO 95/01203.
PCT Published Application WO 95/05452.
PCT Published Application WO 96/02286.
PCT Published Application WO 96/02646.
PCT Published Application WO 96/11698.
PCT Published Application WO 96/40871.
PCT Published Application WO 96/40959.
PCT Published Application WO 97/12635.
PCT Published Application WO 00/23092.

What is claimed is:

1. A substantially pure conotoxin peptide having the general formula I:

Xaa-Xaa$_0$-Xaa$_1$-Cys-Cys-Gly-Xaa$_2$-Xaa$_3$-Xaa$_4$-Cys-Xaa$_5$-Xaa$_6$-Cys-Xaa$_7$ (SEQ E) NO:1), wherein Xaa is des-Xaa, Asn, Gln or pyro-Glu;

Xaa$_0$ is des-Xaa$_0$, Gly, Ala, Glu, γ-carboxy-Glu (Gla) Asp, Asn, Ser, Thr, g-Asn (where g is glycosylation), g-Ser or g-Thr;

Xaa$_1$ is Val, Ala, Gly, Leu, Ile, Ser, Thr, g-Asn, g-Ser or g-Thr;

Xaa$_2$ is Phe, Tyr, meta-Tyr, ortho-Tyr, nor-Tyr, mono-halo-Tyr, di-halo-Tyr, O-sulpho-Tyr, O-phospho-Tyr, nitro-Tyr, Trp (D or L), neo-Trp, halo-Trp (D or L), any non-natural aromatic amino acid, an aliphatic amino acid bearing linear or branched saturated hydrocarbon chains or a non-natural derivative of the aliphatic amino acid;

Xaa$_3$ is Lys, Arg, homolysine, homoarginine, ornithine, nor-Lys, His, N-methyl-Lys, N,N'-dimethyl-Lys, N,N', N"-trimethyl-Lys, any non-natural basic amino acid, Ser, Thr, g-Ser, g-Thr or any non-natural hydroxylated residue;

Xaa$_4$ is an aliphatic amino acid bearing linear or branched saturated hydrocarbon chains or a non-natural derivative of the aliphatic amino acid, Met, Phe, Tyr, meta-Tyr, ortho-Tyr, nor-Tyr, mono-halo-Tyr, di-halo-Tyr, O-sulpho-Tyr, O-phospho-Tyr, nitro-Tyr, Trp (D or L), neo-Trp, halo-Trp (D or L) or any non-natural aromatic amino acid;

Xaa$_5$ is His, Ser, Thr, g-Ser, g-Thr, an aliphatic amino acid bearing linear or branched saturated hydrocarbon chains, a non-natural derivative of the aliphatic amino acid, Phe, Tyr, meta-Tyr, ortho-Tyr, nor-Tyr, mono-halo-Tyr, di-halo-Tyr, O-sulpho-Tyr, O-phospho-Tyr, nitro-Tyr, Trp (D or L), neo-Trp, halo-Trp (D or L) or a non-natural aromatic amino acid;

Xaa$_6$ is Pro, hydroxy-Pro (Hyp) or g-Hyp;

Xaa$_7$ is des-Xaa$_7$, Gly, Ala, Lys,Arg, homolysine, homoarginine, ornithine, nor-Lys, His, N-methyl-Lys, N,N'-dimethyl-Lys, N,N',N"-trimethyl-Lys or any non-natural basic amino acid; and the C-terminus contains a free carboxyl group or an amide group.

2. The substantially pure conotoxin peptide of claim 1 selected from the group consisting of:

Asn-Gly-Val-Cys-Cys-Gly-Xaa$_1$-Xaa$_2$-Leu-Cys-His-Xaa$_3$-Cys (SEQ ID NO:2); and Gly-Val-Cys-Cys-Gly-Xaa$_1$-Xaa$_2$-Leu-Cys-His-Xaa$_3$-Cys (SEQ ID NO:3);

wherein Xaa$_1$ is Tyr, mono-halo-Tyr, di-halo-Tyr, O-sulpho-Tyr, O-phospho-Tyr, nitro-Tyr, Xaa$_2$ is Lys, N-methy-Lys, N,N-dimethyl-Lys or N,N,N-trimethyl-Lys; Xaa$_3$ is Pro or hydroxy-Pro; and the C-terminus contains a carboxyl or amide group.

3. The substantially pure conotoxin peptide of claim 2, wherein Xaa$_1$ is Tyr.

4. The substantially pure conotoxin peptide of claim 2, wherein Xaa$_2$ is Lys.

5. The substantially pure conotoxin peptide of claim 2, wherein Xaa$_3$ is hydroxy-Pro.

6. The substantially pure conotoxin peptide of claim 2, wherein Xaa$_1$ is Tyr, Xaa$_2$ is Lys, and Xaa$_3$ is hydroxy-Pro.

7. The substantially pure conotoxin peptide of claim 2, wherein halo is iodine.

8. The substantially pure conotoxin peptide of claim 7, wherein Xaa$_3$ is mono-iodo-Tyr.

9. The substantially pure conotoxin peptide of claim 7, wherein Xaa$_3$ is di-iodo-Tyr.

10. A substantially pure conotoxin peptide derivative comprising the peptide of claim 2, wherein at least one amino acid residue is substituted, said substitution being selected from the group consisting of an Xaa$_2$ residue substituted by Arg, ornithine, homoarginine, nor-Lys, or any non-natural basic amino acid; a Tyr residue substituted with any non-natural aromatic containing amino acid; a Ser residue substituted with Thr or any non-natural hydroxy containing amino acid; a Thr residue substituted with Ser or any synthetic hydroxy containing amino acid; a Phe residue substituted with any non-natural aromatic amino acid; a Trp residue substituted with any non-natural aromatic amino acid; an Asn residue glycosylated; a Ser residue glycosylated; a Thr residue glycosylated; a Hyp residue glycosylated; a Cys residue in D or L configuration; a Cys residue substituted with homocysteine (D or L); a Tyr residue substituted with the 3-hydroxyl or 2-hydroxyl isomers (meta-Tyr or ortho-Tyr, respectively) and corresponding O-sulpho- and O-phospho-derivatives; an acidic amino acid residue substituted with any non-natural acidic amino acid; a pair of Cys residues replaced pairwise with isoteric lactam or ester-thioether replacements; and an aliphatic amino acid substituted by synthetic derivatives bearing non-natural aliphatic branched or linear side chains $C_nH_{2n+2}$ up to and including n=8.

11. The substantially pure conotoxin peptide of claim 2, wherein said peptide has the sequence set forth in SEQ ID NO:2, wherein Xaa$_1$ is Tyr, Xaa$_2$ is Lys and Xaa$_3$ is hydroxy-Pro.

12. The substantially pure conotoxin peptide of claim 2, wherein said peptide has the sequence set forth in SEQ ID NO:3, wherein Xaa$_1$ is Tyr, Xaa$_2$ is Lys and Xaa$_3$ is hydroxy-Pro.

13. A method for inducing analgesia in a mammal which comprises administering a therapeutically effective amount of a conotoxin peptide of claim 1.

14. The method of claim 13, wherein said administration comprises using a delivery means selected from the group consisting of a pump, microencapsulation, a continuous release polymer implant, macroencapsulation, naked or unencapsulated cell grafts, injection and oral administration.

15. The method of claim 14, wherein administration is intrathecal injection.

16. The method of claim 14, wherein administration is intracerebroventricular injection.

17. The method of claim 14, wherein administration is by pump.

18. The method of claim 14, wherein the amount of conotoxin peptide administered is between about 0.001 mg/kg to about 250 mg/kg.

19. The pharmaceutical composition comprising a therapeutically effective amount of the conotoxin peptide of claim 1 or a pharmaceutically acceptable salt or solvate thereof and a pharmaceutically acceptable carrier.

20. The composition of claim 19 which further comprises one or more drugs useful in the treatment of pain.

21. An isolated conotoxin propeptide having the amino acid sequence set forth in SEQ ID NO:12.

22. The substantially pure conotoxin peptide of claim 1, wherein said aliphatic amino acid bearing linear or branched saturated hydrocarbon chains is Leu (D or L), Ile, or Val.

23. The substantially pure conotoxin peptide derivative of claim 10, wherein said synthetic acidic amino acid is a tetrazolyl derivative of Gly or Ala.

24. The substantially pure conotoxin peptide derivative of claim 10, wherein said isoteric lactam or esterthioether replacements are Ser/(Glu or Asp), Lys/(Glu or Asp), or Cys/Ala combinations.

* * * * *

Adverse Decision in Interference

Patent No. 6,767,896, J. Michael McIntosh, Baldomero M. Olivera, Lourdes J. Cruz, Gloria P. Corpuz, Robert M. Jones, James E. Garrett, CONOTOXIN PEPTIDES, Interference No. 105,492, final judgment adverse to the patentees rendered August 17, 2007, as to claims 1-6, 11, 13-20, and 22.

*(Official Gazette November 27, 2007)*

SEQUENCE LISTING

<160> NUMBER OF SEQ ID NOS: 20

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence:generic
      conotoxin peptide sequence
<221> NAME/KEY: PEPTIDE
<222> LOCATION: (1)..(2)
<223> OTHER INFORMATION: Xaa at residue 1 is des-Xaa, Asn, Gln or pyro-
      Glu; Xaa at residue 2 is des-Xaa, Gly, Ala, Glu, gamma-
      carboxy-Glu, Asp, Asn, Ser, Thr, g-Asn (where g is
      glycosylation), g-Ser or g-Thr;
<221> NAME/KEY: PEPTIDE
<222> LOCATION: (3)..(7)
<223> OTHER INFORMATION: Xaa at residue 3 is Val, Ala, Gly, Leu, Ile,
      Ser, Thr, g-Asn, g-Ser or g-Thr; Xaa at residue 7 is
      Phe, Tyr, meta-Tyr, ortho-Tyr, nor-Tyr,
      mono-halo-Tyr, di-halo-Tyr, O-sulpho-Tyr,
<221> NAME/KEY: PEPTIDE
<222> LOCATION: (7)
<223> OTHER INFORMATION: nitro-Tyr, Trp (D or L), neo-Trp, halo-Trp (D
      or L), any synthetic aromatic amino acid, an
      aliphatic amino acid bearing linear or branched
      saturated hydrocarbon chains such as Leu (D or L),
<221> NAME/KEY: PEPTIDE
<222> LOCATION: (7)..(8)
<223> OTHER INFORMATION: Val or non-natural derivatives of the aliphatic
      amino acid; Xaa at residue 8 is Lys, Arg,
      homolysine, homoarginine, ornithine, nor-Lys, His,
      N-methyl-Lys, N,N'-dimethyl-Lys,
<221> NAME/KEY: PEPTIDE
<222> LOCATION: (8)..(9)
<223> OTHER INFORMATION: any synthetic basic amino acid, Ser, Thr,
      g-Ser, g-Thr or any hydroxylated synthetic residue; Xaa
      at residue 9 is an aliphatic amino acids bearing
      linear or branched saturated hydrocarbon chains
<221> NAME/KEY: PEPTIDE
<222> LOCATION: (9)
<223> OTHER INFORMATION: as Leu (D or L), Ile and Val or non-natural
      derivatives of the aliphatic amino acid, Met, Phe,
      Tyr, meta-Tyr, ortho-Tyr, nor-Tyr, mono-halo-Tyr,
      di-halo-Tyr, O-sulpho-Tyr, O-phospho-Tyr,
<221> NAME/KEY: PEPTIDE
<222> LOCATION: (9)..(11)
<223> OTHER INFORMATION: Trp (D or L), neo-Trp, halo-Trp (D or L) or
      any synthetic aromatic amino acid; Xaa at residue 11
      is His, Ser, Thr, g-Ser, g-Thr, an aliphatic amino
      acid bearing linear or branched saturated
<221> NAME/KEY: NP_BIND
<222> LOCATION: (11)
<223> OTHER INFORMATION: hydrocarbon chains such as Leu (D or L), Ile
      and Val, non-natural derivatives of the aliphatic
      amino acid, Phe, Tyr, meta-Tyr, ortho-Tyr,
      nor-Tyr, mono-halo-Tyr, di-halo-Tyr, O-sulpho-Tyr,
<221> NAME/KEY: PEPTIDE
<222> LOCATION: (11)..(14)
<223> OTHER INFORMATION: O-phospho-Tyr, nitro-Tyr, Trp (D or L),
      neo-Trp, halo-Trp (D or L) or a synthetic aromatic amino
      acid; Xaa at residue 12 is Pro, hydroxy- Pro (Hyp)
      or g-Hyp; Xaa at residue 14 is des-Xaa, Gly, Ala,
<221> NAME/KEY: PEPTIDE
<222> LOCATION: (14)
<223> OTHER INFORMATION: Lys, Arg, homolysine, homoarginine, ornithine,

```
      nor-Lys, His, N-methyl-Lys, N,N'-dimethyl-Lys,
      N,N',N''-trimethyl-Lys or any synthetic basic
      amino acid.

<400> SEQUENCE: 1

Xaa Xaa Xaa Cys Cys Gly Xaa Xaa Xaa Cys Xaa Xaa Cys Xaa
 1               5                  10

<210> SEQ ID NO 2
<211> LENGTH: 13
<212> TYPE: PRT
<213> ORGANISM: Conus marmoreus
<220> FEATURE:
<221> NAME/KEY: PEPTIDE
<222> LOCATION: (7)..(8)
<223> OTHER INFORMATION: Xaa at residue 7 is Tyr, mono-halo-Tyr,
      di-halo-Tyr, O-sulpho-Tyr, O-Phospho-Tyr or
      nitro-Tyr; Xaa at residue 8 is Lys, N-methyl-Lys,
      N,N-dimethyl-Lys or N,N,N-trimethyl Lys
<221> NAME/KEY: PEPTIDE
<222> LOCATION: (12)
<223> OTHER INFORMATION: Xaa at residue 12 is Pro or hydroxy-Pro.

<400> SEQUENCE: 2

Asn Gly Val Cys Cys Gly Xaa Xaa Leu Cys His Xaa Cys
 1               5                  10

<210> SEQ ID NO 3
<211> LENGTH: 12
<212> TYPE: PRT
<213> ORGANISM: Conus marmoreus
<220> FEATURE:
<221> NAME/KEY: PEPTIDE
<222> LOCATION: (6)..(7)
<223> OTHER INFORMATION: Xaa at residue 6 is Tyr, mono-halo-Tyr,
      di-halo-Tyr, O-sulpho-Tyr, O-Phospho-Tyr or
      nitro-Tyr; Xaa at residue 7 is Lys, N-methyl-Lys,
      N,N-dimethyl-Lys or N,N,N-trimethyl Lys
<221> NAME/KEY: PEPTIDE
<222> LOCATION: (11)
<223> OTHER INFORMATION: Xaa at residue 11 is Pro or hydroxy-Pro

<400> SEQUENCE: 3

Gly Val Cys Cys Gly Xaa Xaa Leu Cys His Xaa Cys
 1               5                  10

<210> SEQ ID NO 4
<211> LENGTH: 12
<212> TYPE: PRT
<213> ORGANISM: Unknown
<220> FEATURE:
<223> OTHER INFORMATION: Description of Unknown Organism:unknown Conus
      species
<221> NAME/KEY: PEPTIDE
<222> LOCATION: (6)..(7)
<223> OTHER INFORMATION: Xaa at residue 6 is Tyr, mono-halo-Tyr,
      di-halo-Tyr, O-sulpho-Tyr, O-Phospho-Tyr or
      nitro-Tyr; Xaa at residue 8 is Lys, N-methyl-Lys,
      N,N-dimethyl-Lys or N,N,N-trimethyl Lys.
<221> NAME/KEY: PEPTIDE
<222> LOCATION: (11)
<223> OTHER INFORMATION: Xaa at residue 11 is Pro or hydroxy-Pro

<400> SEQUENCE: 4

Gly Val Cys Cys Gly Xaa Xaa Leu Cys His Xaa Cys
 1               5                  10

<210> SEQ ID NO 5
<211> LENGTH: 11
<212> TYPE: PRT
<213> ORGANISM: Conus bandanus
```

```
<220> FEATURE:
<221> NAME/KEY: PEPTIDE
<222> LOCATION: (5)..(6)
<223> OTHER INFORMATION: Xaa at residue 5 is Tyr, mono-halo-Tyr,
      di-halo-Tyr, O-sulpho-Tyr, O-phospho-Tyr,
      nitro-Tyr; Xaa at residue 6 is Lys, N-methy-Lys,
      N,N-dimethyl-Lys or N,N,N-trimethyl-Lys;
<221> NAME/KEY: PEPTIDE
<222> LOCATION: (10)
<223> OTHER INFORMATION: Xaa at residue 10 is Pro or hydroxy-Pro (Hyp)

<400> SEQUENCE: 5

Ala Cys Cys Gly Xaa Xaa Lys Cys Ser Xaa Cys
 1               5                  10

<210> SEQ ID NO 6
<211> LENGTH: 13
<212> TYPE: PRT
<213> ORGANISM: Conus textile
<220> FEATURE:
<221> NAME/KEY: PEPTIDE
<222> LOCATION: (1)..(11)
<223> OTHER INFORMATION: Xaa at residue 1 is Gln or pyro-Glu; Xaa at
      residue 6 is Tyr, mono-halo-Tyr, di-halo-Tyr,
      O-sulpho-Tyr, O-phospho-Tyr, nitro-Tyr; Xaa at
      residue 11 is Pro or hydroxy-Pro (Hyp)

<400> SEQUENCE: 6

Xaa Thr Cys Cys Gly Xaa Arg Met Cys Val Xaa Cys Gly
 1               5                  10

<210> SEQ ID NO 7
<211> LENGTH: 13
<212> TYPE: PRT
<213> ORGANISM: Conus pennaceus
<220> FEATURE:
<221> NAME/KEY: PEPTIDE
<222> LOCATION: (7)..(11)
<223> OTHER INFORMATION: Xaa at residue 7 is Lys, N-methy-Lys,
      N,N-dimethyl-Lys or N,N,N-trimethyl-Lys; Xaa at
      residue 11 is Pro or hydroxy-Pro (Hyp)

<400> SEQUENCE: 7

Ser Thr Cys Cys Gly Phe Xaa Met Cys Ile Xaa Cys Arg
 1               5                  10

<210> SEQ ID NO 8
<211> LENGTH: 25
<212> TYPE: DNA
<213> ORGANISM: Conus marmoreus
<220> FEATURE:
<221> NAME/KEY: modified_base
<222> LOCATION: (14)
<223> OTHER INFORMATION: i

<400> SEQUENCE: 8
caggatccaa yggngtbtgy tgygg                                        25

<210> SEQ ID NO 9
<211> LENGTH: 28
<212> TYPE: DNA
<213> ORGANISM: Conus marmoreus
<220> FEATURE:
<221> NAME/KEY: modified_base
<222> LOCATION: (26)
<223> OTHER INFORMATION: i

<400> SEQUENCE: 9
ctggatccgg rtgrcavary ttrtancc                                     28
```

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:universal
      primer

<400> SEQUENCE: 10
aagctcgagt aacaacgcag agt                                         23

<210> SEQ ID NO 11
<211> LENGTH: 805
<212> TYPE: DNA
<213> ORGANISM: Conus marmoreus
<220> FEATURE:
<221> NAME/KEY: CDS
<222> LOCATION: (82)..(264)

<400> SEQUENCE: 11
ggcgaataca cctggcaggt actcaacgaa cttcaggaca cattcttttc acctggacac    60
tggaaactga caacaggcag a atg cgc tgt ctc cca gtc ttg atc att ctt    111
                        Met Arg Cys Leu Pro Val Leu Ile Ile Leu
                         1               5                  10 ctg ctg ctg act gca tct gca cct ggc gtt gtt gtc cta ccg aag acc    159
Leu Leu Leu Thr Ala Ser Ala Pro Gly Val Val Val Leu Pro Lys Thr
             15                  20                  25 gaa gat gat gtg ccc atg tca tct gtc tac ggt aat gga aag agt atc    207
Glu Asp Asp Val Pro Met Ser Ser Val Tyr Gly Asn Gly Lys Ser Ile
         30                  35                  40 cta cga gga att ctg agg aac ggt gtt tgc tgt ggc tat aag ttg tgc    255
Leu Arg Gly Ile Leu Arg Asn Gly Val Cys Cys Gly Tyr Lys Leu Cys
     45                  50                  55 cat cca tgt taaccagcat gaagggaaat gactttggat gagacccctg            304
His Pro Cys
         60 cgaactgtcc ctggatgtga aatttggaaa gcagactgtt cctttcgcac gtattcgtgg   364 aatttcgaat ggtcgtaaac aacacgctgc cacttgcagg ctactatctc tctgtccttt   424 catctgtgga aatggatgat ctaacaactg aaatatcaga aatttttcaa tggctataca   484 ctatgaccat gtagtcagta attatatcat ttggaccttt tgaaatattt ttcaatatgt   544 aaagttttg caccctggaa aggtcttttg gagttaaata ttttagtatg ttatgttttg    604 catacaagtt atagaatgct gtctttcttt tgttcccac atcaatggtg ggggcagaaa    664 ttatttgttt tggtcaatgt aattatgacc tgcatttagt gctatagtga ttgcattttc   724 agcgtggaat gtttaatctg caaacagaaa gtggttgatc gactaataaa gatttgcatg   784 gcacaaaaaa aaaaaaaaaa a                                            805

<210> SEQ ID NO 12
<211> LENGTH: 61
<212> TYPE: PRT
<213> ORGANISM: Conus marmoreus

<400> SEQUENCE: 12

Met Arg Cys Leu Pro Val Leu Ile Ile Leu Leu Leu Leu Thr Ala Ser
 1               5                  10                  15

Ala Pro Gly Val Val Val Leu Pro Lys Thr Glu Asp Asp Val Pro Met
             20                  25                  30

Ser Ser Val Tyr Gly Asn Gly Lys Ser Ile Leu Arg Gly Ile Leu Arg

-continued

```
                35                  40                  45
Asn Gly Val Cys Cys Gly Tyr Lys Leu Cys His Pro Cys
         50                  55                  60
```

<210> SEQ ID NO 13
<211> LENGTH: 202
<212> TYPE: DNA
<213> ORGANISM: Conus bandanus
<220> FEATURE:
<221> NAME/KEY: CDS
<222> LOCATION: (1)..(183)

<400> SEQUENCE: 13

```
atg cgc tgt ctc cca gtc ttg atc att ctt ctg ctg act gca tct            48
Met Arg Cys Leu Pro Val Leu Ile Ile Leu Leu Leu Thr Ala Ser
 1               5                  10                  15 gca cct ggc gtt gat gtc cta ccg aag acc gaa gat gat gtg ccc ctg        96
Ala Pro Gly Val Asp Val Leu Pro Lys Thr Glu Asp Asp Val Pro Leu
             20                  25                  30 tca tct gtc tac gat aat aca aag agt atc cta cga gga ctt ctg gac      144
Ser Ser Val Tyr Asp Asn Thr Lys Ser Ile Leu Arg Gly Leu Leu Asp
         35                  40                  45 aaa cgt gct tgc tgt ggc tac aag ctt tgc tca cca tgt taaccagcat       193
Lys Arg Ala Cys Cys Gly Tyr Lys Leu Cys Ser Pro Cys
 50                  55                  60 gaaggatcc                                                             202
```

<210> SEQ ID NO 14
<211> LENGTH: 61
<212> TYPE: PRT
<213> ORGANISM: Conus bandanus

<400> SEQUENCE: 14

```
Met Arg Cys Leu Pro Val Leu Ile Ile Leu Leu Leu Thr Ala Ser
 1               5                  10                  15

Ala Pro Gly Val Asp Val Leu Pro Lys Thr Glu Asp Asp Val Pro Leu
             20                  25                  30

Ser Ser Val Tyr Asp Asn Thr Lys Ser Ile Leu Arg Gly Leu Leu Asp
         35                  40                  45

Lys Arg Ala Cys Cys Gly Tyr Lys Leu Cys Ser Pro Cys
 50                  55                  60
```

<210> SEQ ID NO 15
<211> LENGTH: 205
<212> TYPE: DNA
<213> ORGANISM: Conus textile
<220> FEATURE:
<221> NAME/KEY: CDS
<222> LOCATION: (1)..(186)

<400> SEQUENCE: 15

```
atg cac tgt ctc cca atc ttc gtc att ctt ctg ctg ctg act gca tct        48
Met His Cys Leu Pro Ile Phe Val Ile Leu Leu Leu Leu Thr Ala Ser
 1               5                  10                  15 gga cct agc gtt gat gcc caa ctg aag acc aaa gat gat gtg ccc ctg        96
Gly Pro Ser Val Asp Ala Gln Leu Lys Thr Lys Asp Asp Val Pro Leu
             20                  25                  30 tca tct ttc cga gat cat gca aag agt acc cta cga aga ctt cag gac      144
Ser Ser Phe Arg Asp His Ala Lys Ser Thr Leu Arg Arg Leu Gln Asp
         35                  40                  45 aaa cag act tgc tgt ggc tat agg atg tgt gtt cct tgt ggt              186
Lys Gln Thr Cys Cys Gly Tyr Arg Met Cys Val Pro Cys Gly
```

```
               50                  55                  60 taaccagcat gaaggatcc                                                    205

<210> SEQ ID NO 16
<211> LENGTH: 62
<212> TYPE: PRT
<213> ORGANISM: Conus textile

<400> SEQUENCE: 16

Met His Cys Leu Pro Ile Phe Val Ile Leu Leu Leu Thr Ala Ser
  1               5                  10                  15

Gly Pro Ser Val Asp Ala Gln Leu Lys Thr Lys Asp Val Pro Leu
                 20                  25                  30

Ser Ser Phe Arg Asp His Ala Lys Ser Thr Leu Arg Arg Leu Gln Asp
             35                  40                  45

Lys Gln Thr Cys Cys Gly Tyr Arg Met Cys Val Pro Cys Gly
         50                  55                  60

<210> SEQ ID NO 17
<211> LENGTH: 211
<212> TYPE: DNA
<213> ORGANISM: Conus pennaceus
<220> FEATURE:
<221> NAME/KEY: CDS
<222> LOCATION: (1)..(189)

<400> SEQUENCE: 17 atg cgc tgt ctc cca gtc ttc gtc att ctt ctg ctg act gca tct         48
Met Arg Cys Leu Pro Val Phe Val Ile Leu Leu Leu Thr Ala Ser
  1               5                  10                  15 gca cct agc gtt gat gcc aaa gtt cat ctg aag acc aaa ggt gat ggg      96
Ala Pro Ser Val Asp Ala Lys Val His Leu Lys Thr Lys Gly Asp Gly
             20                  25                  30 ccc ctg tca tct ttc cga gat aat gca aag agt acc cta caa aga ctt    144
Pro Leu Ser Ser Phe Arg Asp Asn Ala Lys Ser Thr Leu Gln Arg Leu
         35                  40                  45 cag gac aaa agc act tgc tgt ggc ttt aag atg tgt att cct tgt        189
Gln Asp Lys Ser Thr Cys Cys Gly Phe Lys Met Cys Ile Pro Cys
     50                  55                  60 cgttaaccag catgaaggat cc                                            211

<210> SEQ ID NO 18
<211> LENGTH: 63
<212> TYPE: PRT
<213> ORGANISM: Conus pennaceus

<400> SEQUENCE: 18

Met Arg Cys Leu Pro Val Phe Val Ile Leu Leu Leu Thr Ala Ser
  1               5                  10                  15

Ala Pro Ser Val Asp Ala Lys Val His Leu Lys Thr Lys Gly Asp Gly
             20                  25                  30

Pro Leu Ser Ser Phe Arg Asp Asn Ala Lys Ser Thr Leu Gln Arg Leu
         35                  40                  45

Gln Asp Lys Ser Thr Cys Cys Gly Phe Lys Met Cys Ile Pro Cys
     50                  55                  60

<210> SEQ ID NO 19
<211> LENGTH: 24
<212> TYPE: DNA
<213> ORGANISM: Conus marmoreus
```

```
<400> SEQUENCE: 19
ggaattcgga agctgactac aagc                                              24

<210> SEQ ID NO 20
<211> LENGTH: 22
<212> TYPE: DNA
<213> ORGANISM: Conus marmoreus

<400> SEQUENCE: 20
ctggatcctt catgctggtt aa                                                22
```